(12) United States Patent
Hiraoka

(10) Patent No.: US 8,517,949 B2
(45) Date of Patent: Aug. 27, 2013

(54) ULTRASOUND TRANSDUCER UNIT AND ULTRASOUND ENDOSCOPE

(71) Applicant: Olympus Medical Systems Corp., Tokyo (JP)

(72) Inventor: Jin Hiraoka, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/675,321

(22) Filed: Nov. 13, 2012

(65) Prior Publication Data

US 2013/0072801 A1    Mar. 21, 2013

Related U.S. Application Data

(63) Continuation of application No. PCT/JP2012/059098, filed on Apr. 3, 2012.

(30) Foreign Application Priority Data

May 13, 2011    (JP) ................................. 2011-108510

(51) Int. Cl.
  *A61B 8/14*    (2006.01)
(52) U.S. Cl.
  USPC ............................ 600/459; 600/437; 310/311
(58) Field of Classification Search
  USPC .................. 600/437–472; 310/311
  See application file for complete search history.

(56) References Cited

U.S. PATENT DOCUMENTS

| | | | |
|---|---|---|---|
| 2004/0073118 A1* | 4/2004 | Peszynski et al. | 600/459 |
| 2006/0058676 A1 | 3/2006 | Yagi et al. | |
| 2006/0241467 A1* | 10/2006 | Takeda et al. | 600/459 |
| 2008/0089181 A1* | 4/2008 | Adachi et al. | 367/189 |
| 2008/0119738 A1* | 5/2008 | Imahashi et al. | 600/462 |

FOREIGN PATENT DOCUMENTS

| | | |
|---|---|---|
| EP | 1 498 071 A1 | 1/2005 |
| JP | 2001-333494 | 11/2001 |
| JP | 2003-033354 | 2/2003 |
| JP | 2004-290273 | 10/2004 |
| JP | 2006-025892 | 2/2006 |
| JP | 2008-289910 | 12/2008 |

(Continued)

OTHER PUBLICATIONS

Light, E.D., et al. "New Fabrication Techniques for Ring-Array Transducers for Real-Time 3D Intravascular Ultrasound", Ultrasonic Imaging 31, Oct. 1, 2009, pp. 247-256.

(Continued)

*Primary Examiner* — James Kish
(74) *Attorney, Agent, or Firm* — Scully, Scott, Murphy & Presser, P.C.

(57) ABSTRACT

An ultrasound transducer unit includes: an ultrasound element; a substrate; a signal transmission cable; a cylindrical metal shield member that has a large-diameter portion, a small-diameter portion, and a step portion, in which the large-diameter portion covers an outer circumference of the substrate; ground wiring that electrically connects the substrate and an outer circumferential face of the metal shield member; and an opening portion formed in the step portion or the small-diameter portion. The ground wiring is extended to outside the metal shield member from inside the large-diameter portion through the opening portion, and is electrically connected to an outer circumferential face of the small-diameter portion to thereby electrically connect the substrate and the outer circumferential face of the metal shield member.

3 Claims, 14 Drawing Sheets

(56) References Cited

FOREIGN PATENT DOCUMENTS

| | | |
|---|---|---|
| JP | 2009-165509 | 7/2009 |
| WO | 99/24967 A1 | 5/1999 |
| WO | WO 03/086196 A1 | 10/2003 |
| WO | WO 2004/084734 A1 | 10/2004 |
| WO | WO 2009/137403 A1 | 11/2009 |

OTHER PUBLICATIONS

European Search Report dated Jun. 17, 2013 from corresponding European Application No. 12 78 5538.5.

* cited by examiner

ULTRASOUND TRANSDUCER UNIT AND ULTRASOUND ENDOSCOPE

CROSS REFERENCE TO RELATED APPLICATION

This application is a continuation application of PCT/JP2012/059098 filed on Apr. 3, 2012 and claims benefit of Japanese Application No. 2011-108510 filed in Japan on May 13, 2011, the entire contents of which are incorporated herein by this reference.

BACKGROUND OF THE INVENTION

1. Field of the Invention

The present invention relates to an ultrasound transducer unit and an ultrasound endoscope equipped with a metal shield member that covers an outer circumference of a substrate that electrically connects an ultrasound element and a signal transmission cable.

2. Description of the Related Art

In an ultrasound endoscope with which it is possible to observe an ultrasound image that is a two-dimensional visible image of a site to be examined, an ultrasound transducer that is provided on a distal end side of an insertion portion normally has a configuration that includes a GND electrode provided on a top face of an ultrasound element such as a single-plate piezoelectric element, and a signal electrode provided on a bottom face of the ultrasound element. The ultrasound transducer has a function that, by application of a voltage from outside to the electrodes on the top and bottom faces of the ultrasound element, radiates ultrasound that accompanies vibration of the ultrasound element towards a site to be examined, and receives a reflected acoustic wave from the site to be examined and converts the reflected acoustic wave into an electrical signal.

Further, a configuration is known in which transferring of at least electric power and electrical signals between the ultrasound transducer and an external device is performed through a signal transmission cable that is inserted through the inside of an insertion portion of the ultrasound endoscope and is electrically connected to the signal electrode of the ultrasound element, within a transducer case that holds the ultrasound transducer.

Note that the signal transmission cable includes a plurality of cables in which the electrical safety is ensured by providing a signal wire and a GND wire that is positioned on an outer layer of the signal wire on the same axis.

In this case, a configuration is also known in which electrical connection of a signal transmission cable to an ultrasound element is performed through a substrate, as disclosed, for example, in Japanese Patent Application Laid-Open Publication No. 2006-25892.

Further, since it is necessary from the viewpoint of electrical safety to also securely cover an exposed area of an electrode in the substrate or the ultrasound element, such as an electrode to which the signal transmission cable is connected in the substrate and an electrode to which the substrate is connected in the ultrasound element, in Japanese Patent Application Laid-Open Publication No. 2006-25892 a configuration is disclosed in which, inside a transducer case that holds an ultrasound transducer, the substrate is hermetically sealed and covered from outside using a metal shield member that is grounded.

Note that, hereunder, a structure in which a metal shield member is covered over the outside of a substrate in a state in which a signal transmission cable is electrically connected to the substrate inside a transducer case is referred to as an "ultrasound transducer unit."

As a configuration for grounding a metal shield member, a configuration is known in which the other end of ground wiring having one end electrically connected to a GND pattern provided on a substrate inside the metal shield member is led out to outside of the metal shield member from inside the metal shield member through an opening in a rear end of the metal shield member before hermetic sealing is performed, and the aforementioned other end is connected by a solder or the like to an outer circumferential face of the metal shield to thereby perform grounding.

SUMMARY OF THE INVENTION

An ultrasound transducer unit according to one aspect of the present invention includes: an ultrasound element; a substrate having one end that is electrically connected to the ultrasound element; a signal transmission cable that is electrically connected to the other end of the substrate; a cylindrical metal shield member that has a large-diameter portion, a small-diameter portion that has a smaller diameter than a diameter of the large-diameter portion, and a step portion that connects the large-diameter portion and the small-diameter portion, in which an opening portion is formed in the step portion or the small-diameter portion, and in which the large-diameter portion covers an outer circumference of the substrate; and ground wiring that electrically connects the substrate and an outer circumferential face on an opposite side to an inner surface that faces the substrate of the metal shield member; wherein the ground wiring electrically connects the substrate and the outer circumferential face of the metal shield member by being extended to outside the metal shield member from inside the large-diameter portion of the metal shield member through the opening portion and electrically connected to the outer circumferential face of the small-diameter portion.

Further, an ultrasound endoscope according to another aspect of the present invention includes the ultrasound transducer unit according to claim 1 at a distal end in an insertion direction of an insertion portion that is inserted into a subject.

DETAILED DESCRIPTION OF THE PREFERRED EMBODIMENT

An embodiment of the present invention is described hereunder with reference to the drawings. It should be noted that the drawings are schematic ones in which the relationship between the thickness and width of each member, the thickness ratios of the members, and the like are different from those of actual members. Naturally, the drawings include portions in which the dimensional relationships and ratios are different from one another.

Figure 1:
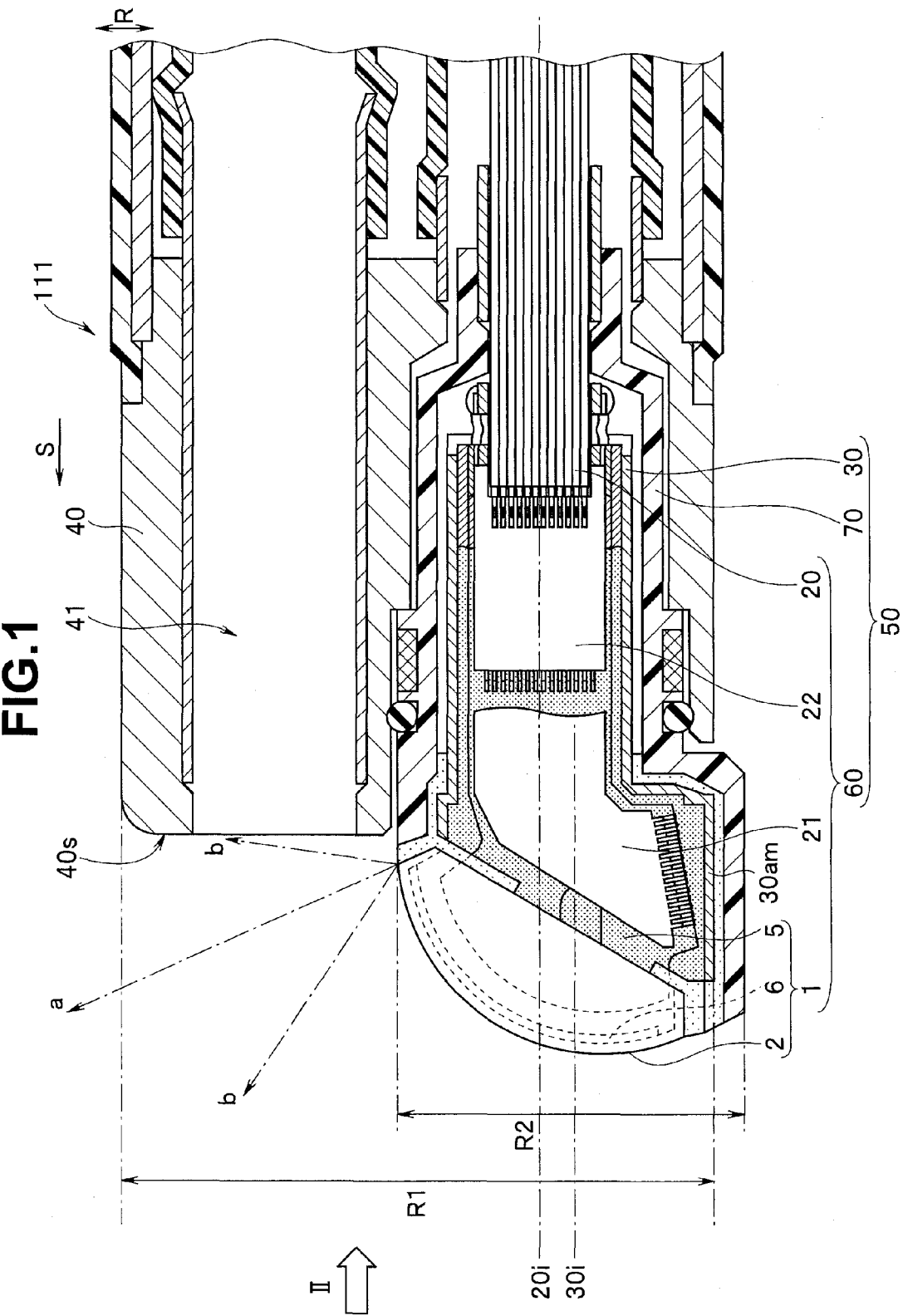
FIG. 1 is a partial cross-sectional view showing a distal end side of an insertion portion of an ultrasound endoscope including an ultrasound transducer unit according to an embodiment of the present invention.
Figure 2:
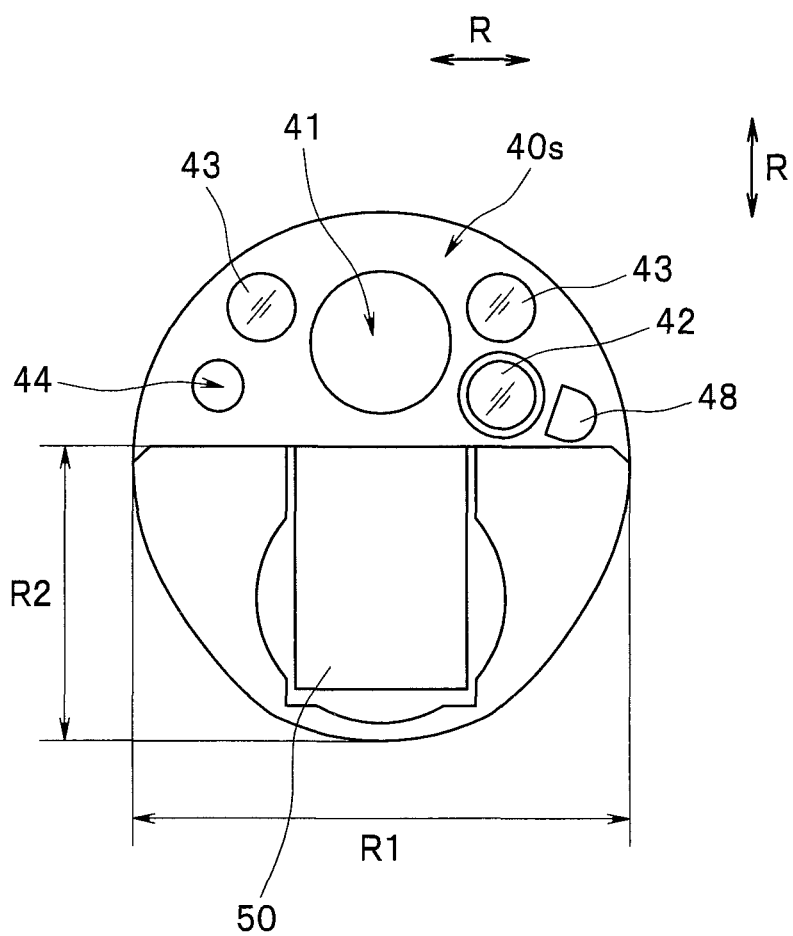
FIG. 2 is a front view of the distal end of the insertion portion shown in FIG. 1 as viewed from a direction II in FIG. 1.
Figure 3:
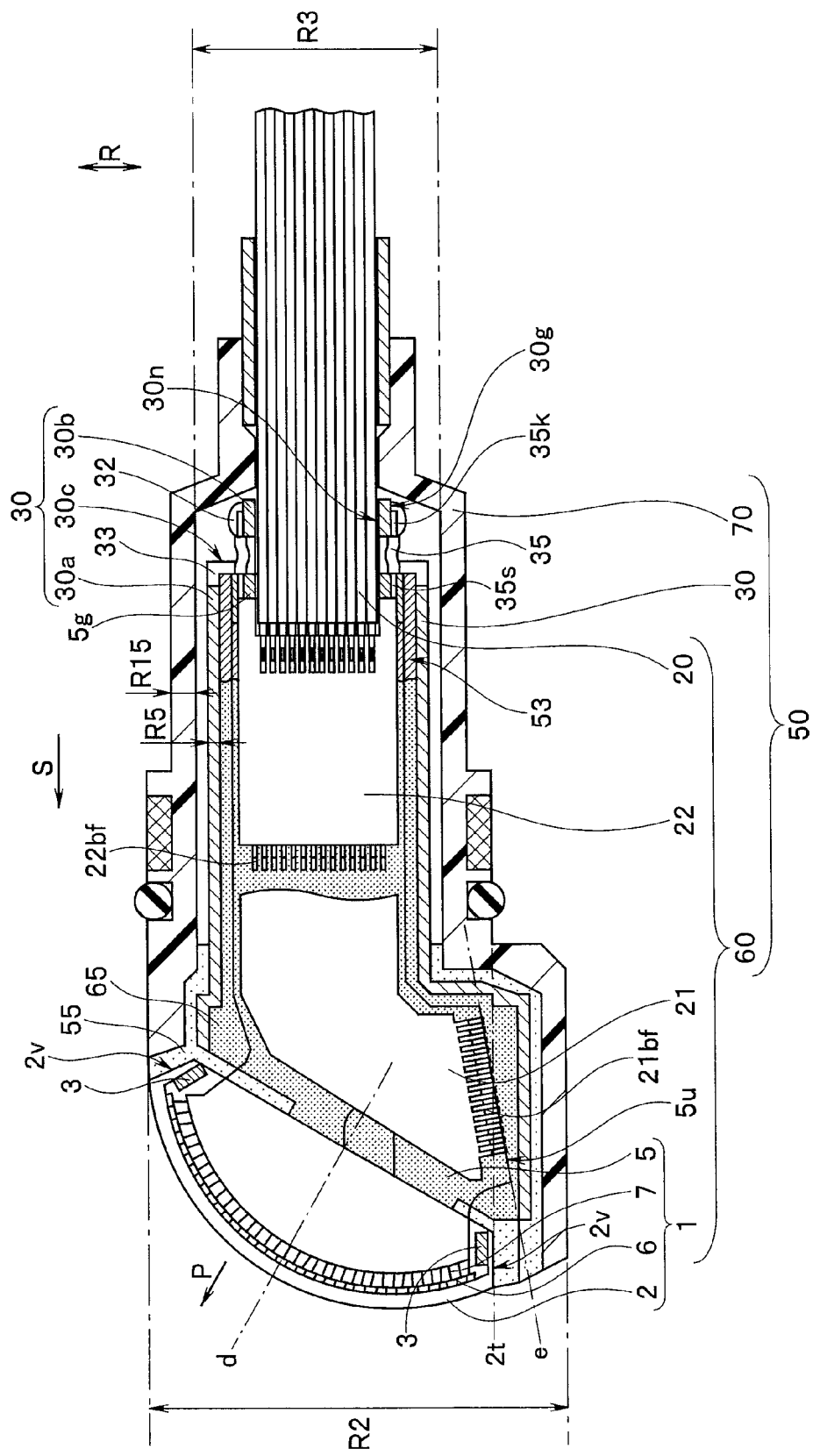
FIG. 3 is a partial cross-sectional view that illustrates the ultrasound transducer unit shown in FIG. 1 in an enlarged manner.

FIG. 1 is a partial cross-sectional view showing a distal end side of an insertion portion of an ultrasound endoscope including an ultrasound transducer unit according to the present embodiment. FIG. 2 is a front view of the distal end of the insertion portion shown in FIG. 1 as viewed from a direction II in FIG. 1. FIG. 3 is a partial cross-sectional view that illustrates the ultrasound transducer unit shown in FIG. 1 in an enlarged manner.

Figure 4:
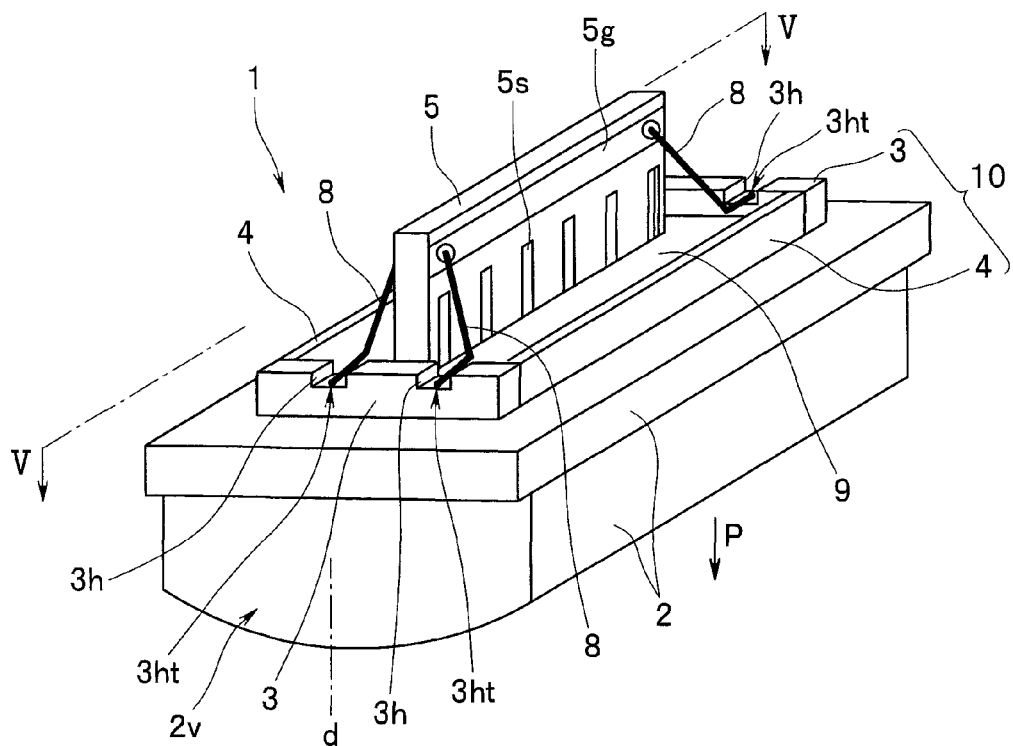
FIG. 4 is a perspective view that illustrates the ultrasound transducer shown in FIG. 1 in an enlarged manner.
Figure 5:
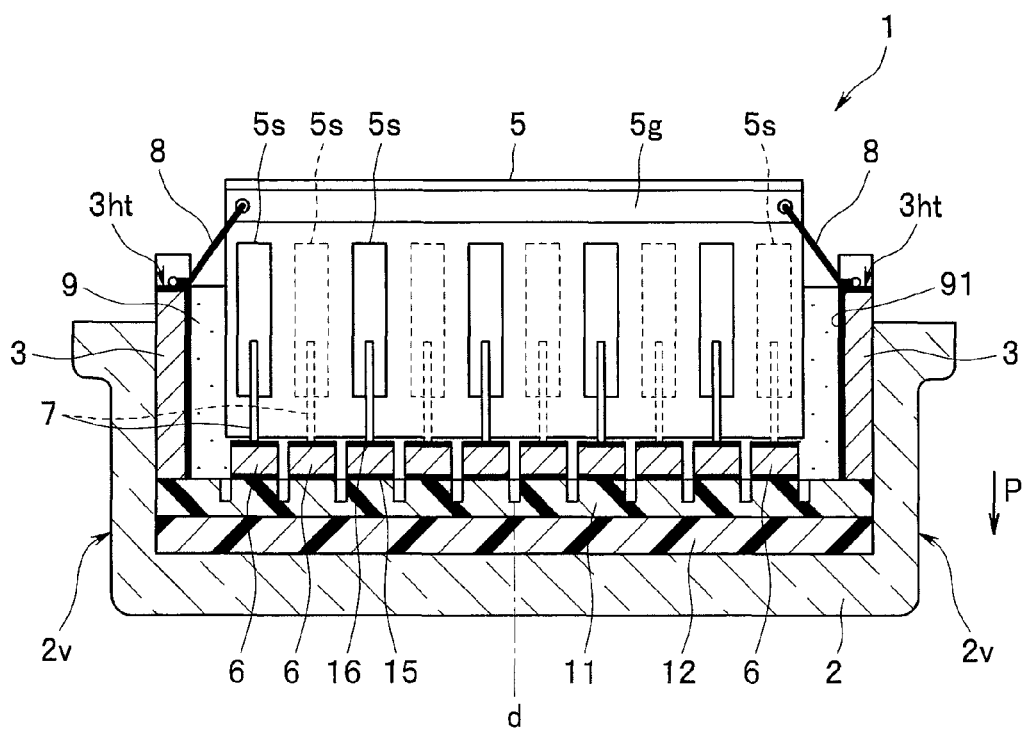
FIG. 5 is a sectional view of the ultrasound transducer along a line V-V in FIG. 4.
Figure 6:
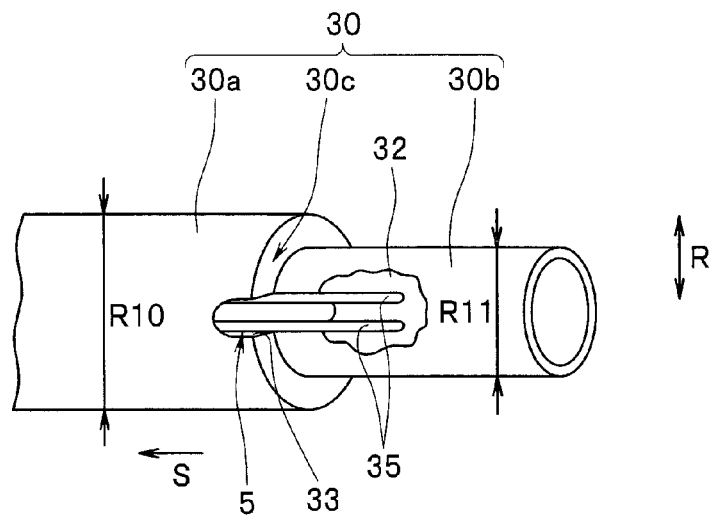
FIG. 6 is a partial enlarged perspective view that illustrates a rear end side of a metal shield member shown in FIG. 1.
Figure 7:
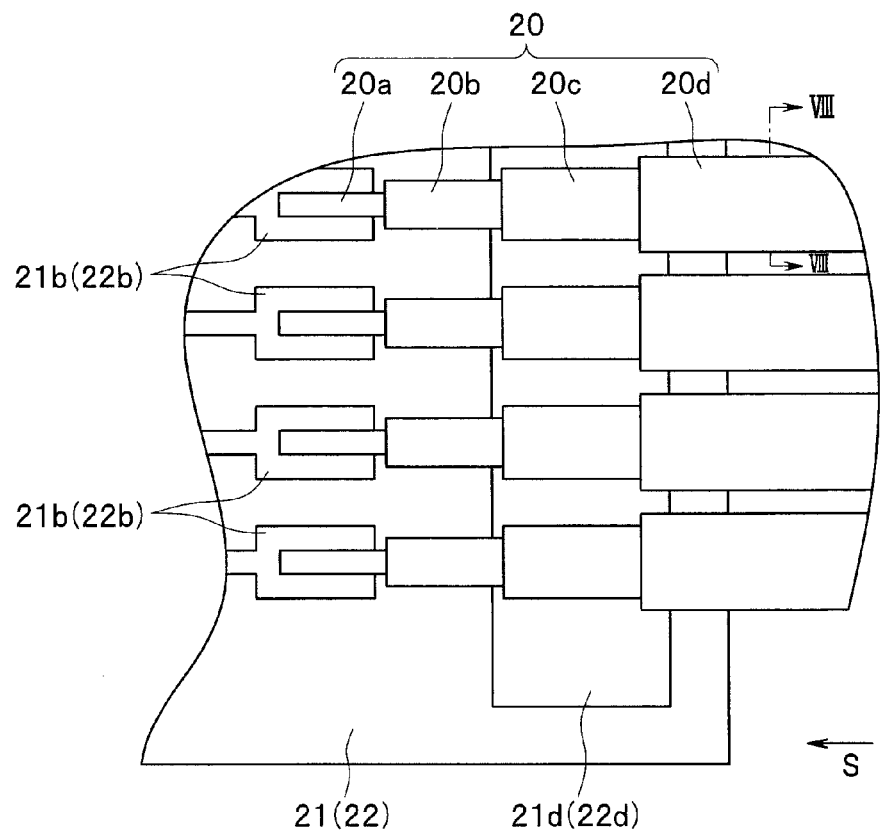
FIG. 7 is a view that illustrates a connection of a signal transmission cable to a flexible substrate shown in FIG. 1 in an enlarged manner.
Figure 8:
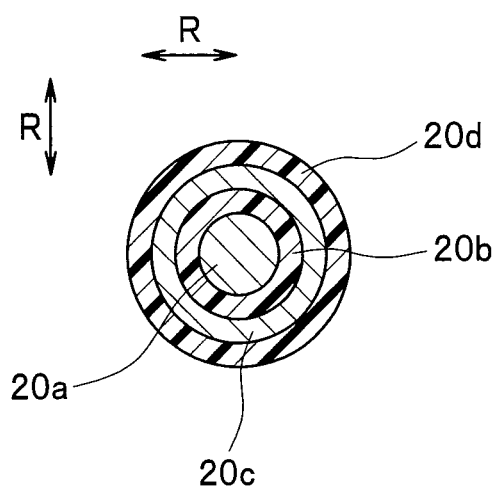
FIG. 8 is a sectional view of a single coaxial line of the signal transmission cable along a line VIII-VIII in FIG. 7.

FIG. 4 is a perspective view that illustrates the ultrasound transducer shown in FIG. 1 in an enlarged manner. FIG. 5 is a sectional view of the ultrasound transducer along a line V-V in FIG. 4. FIG. 6 is a partial enlarged perspective view that illustrates a rear end side of a metal shield member shown in FIG. 1. FIG. 7 is a view that illustrates a connection of a signal transmission cable to a flexible substrate shown in FIG. 1 in an enlarged manner. FIG. 8 is a sectional view of a single coaxial line of the signal transmission cable along a line VIII-VIII in FIG. 7.

Figure 9:
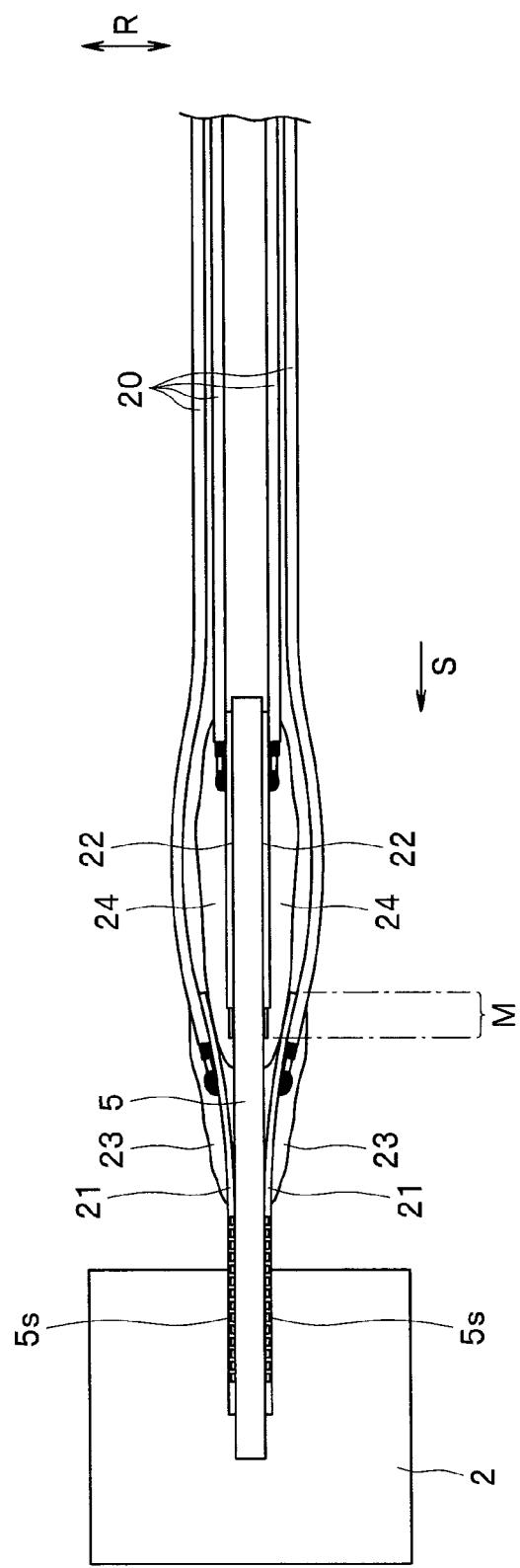
FIG. 9 is a view that illustrates, in an enlarged manner, a connection of the flexible substrate to which the signal transmission cable is connected, to the substrate that is shown in FIG. 1.
Figure 10:
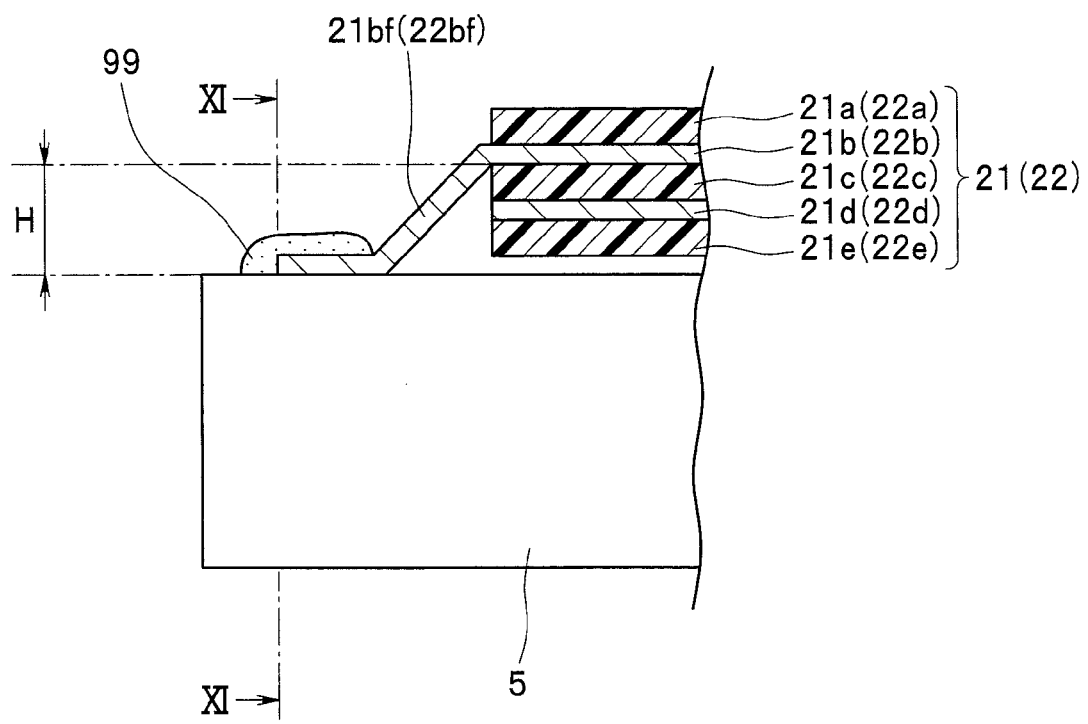
FIG. 10 is a partial cross-sectional view that illustrates the connection of the flexible substrate to the substrate that is shown in FIG. 9 in an enlarged manner.
Figure 11:
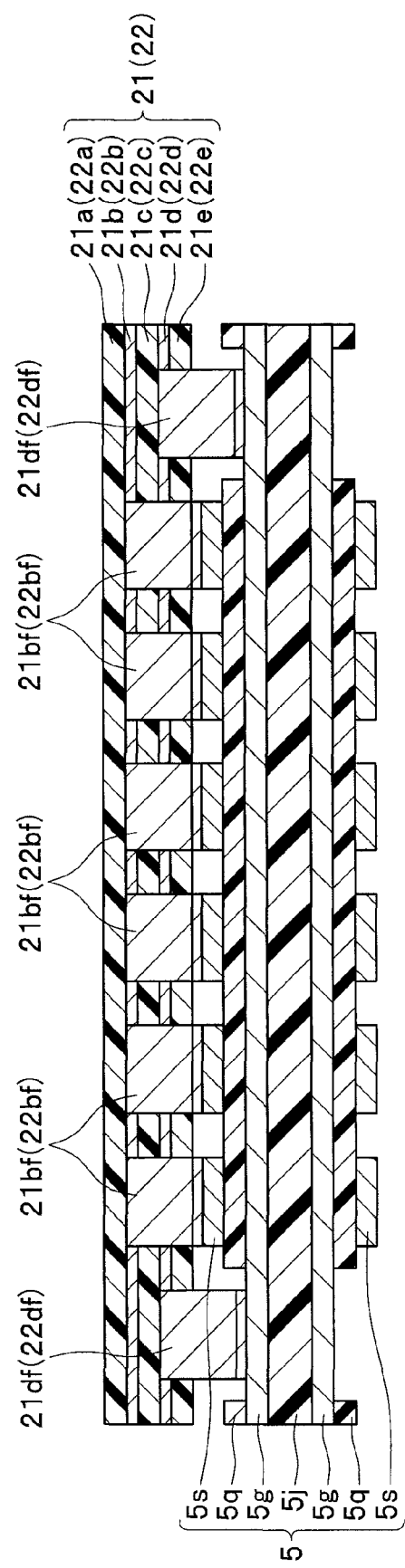
FIG. 11 is a sectional view of the substrate and the flexible substrate along a line XI-XI in FIG. 10.

FIG. 9 is a view that illustrates, in an enlarged manner, a connection of the flexible substrate to which the signal transmission cable is connected, to the substrate that is shown in FIG. 1. FIG. 10 is a partial cross-sectional view that illustrates the connection of the flexible substrate to the substrate that is shown in FIG. 9 in an enlarged manner FIG. 11 is a sectional view of the substrate and the flexible substrate along a line XI-XI in FIG. 10.

Figure 12:
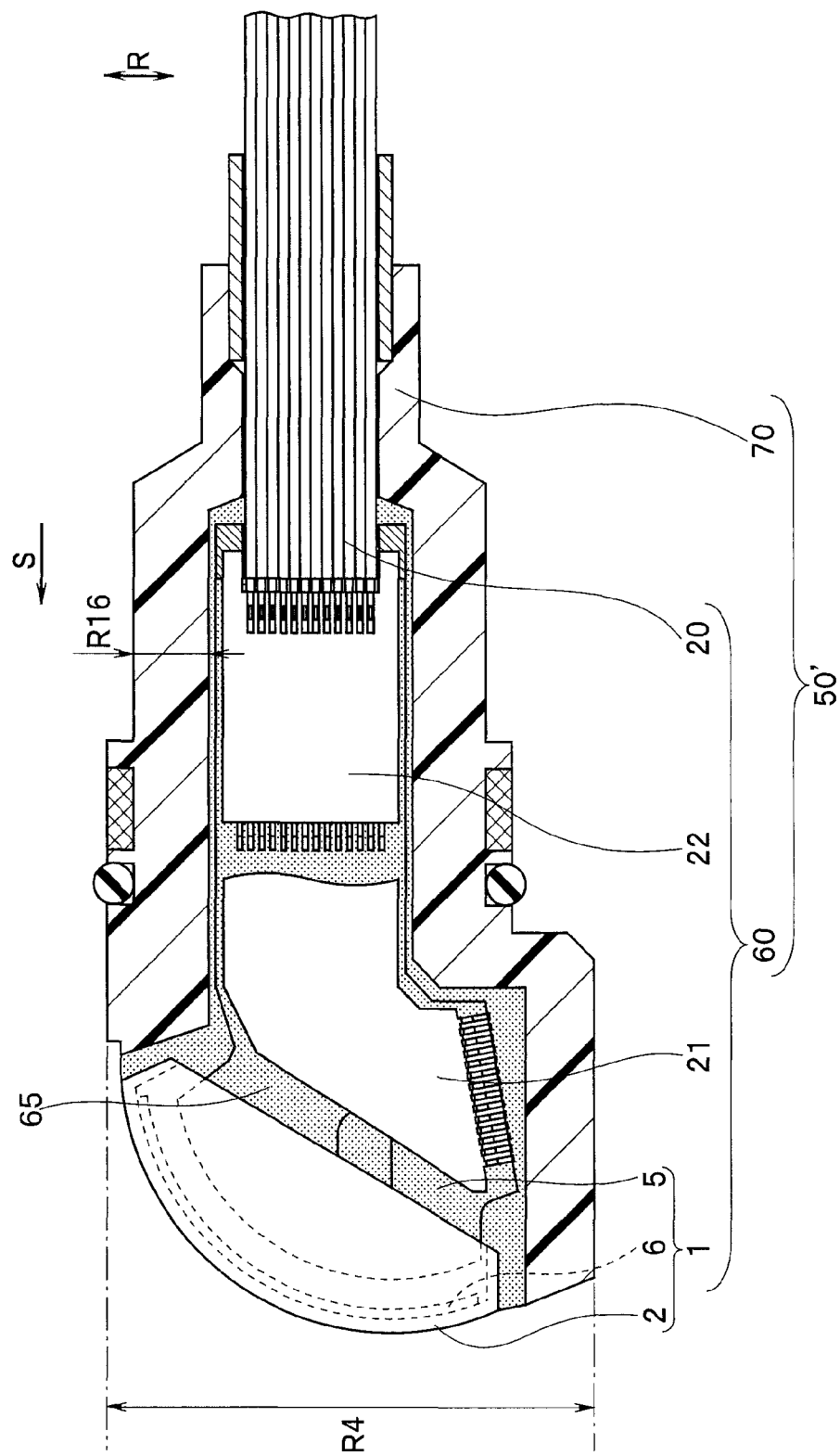
FIG. 12 is a partial cross-sectional view that illustrates, in an enlarged manner, an ultrasound transducer unit that has a configuration that does not use a metal shield member.
Figure 13:
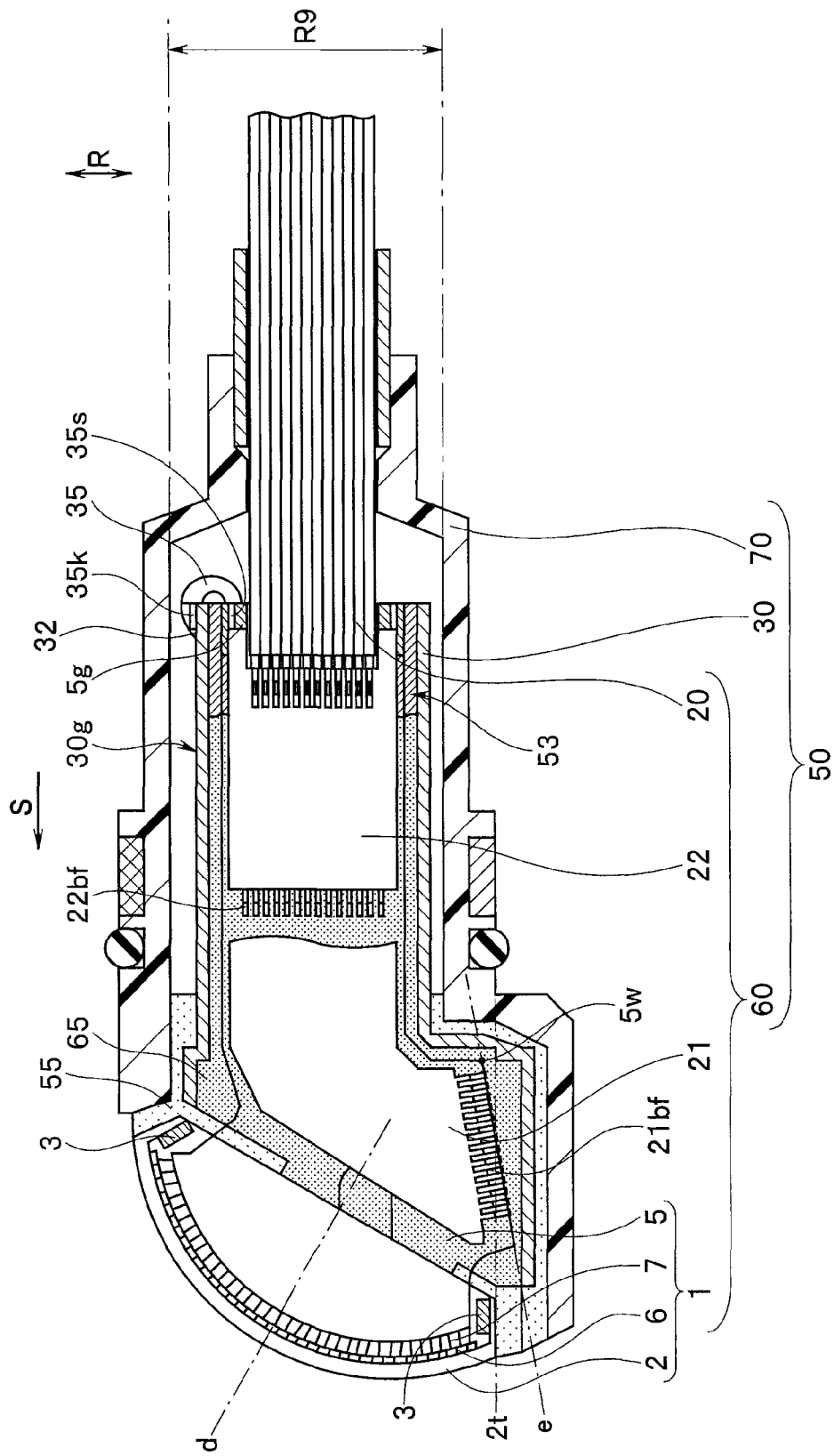
FIG. 13 is a partial cross-sectional view that illustrates a conventional example in which the other end of ground wiring that has one end connected to a ground wiring land of a substrate is led out to outside a metal shield member from inside the metal shield member through an opening in a rear end of the metal shield member, and connected by a solder or the like to an outer circumferential face of the metal shield member.

FIG. 12 is a partial cross-sectional view that illustrates, in an enlarged manner, an ultrasound transducer unit that has a configuration that does not use a metal shield member. FIG. 13 is a partial cross-sectional view that illustrates a conventional example in which the other end of ground wiring that has one end connected to a ground wiring land of a substrate is led out to outside a metal shield member from inside the metal shield member through an opening in a rear end of the metal shield member, and connected by a solder or the like to an outer circumferential face of the metal shield member.

Figure 14:
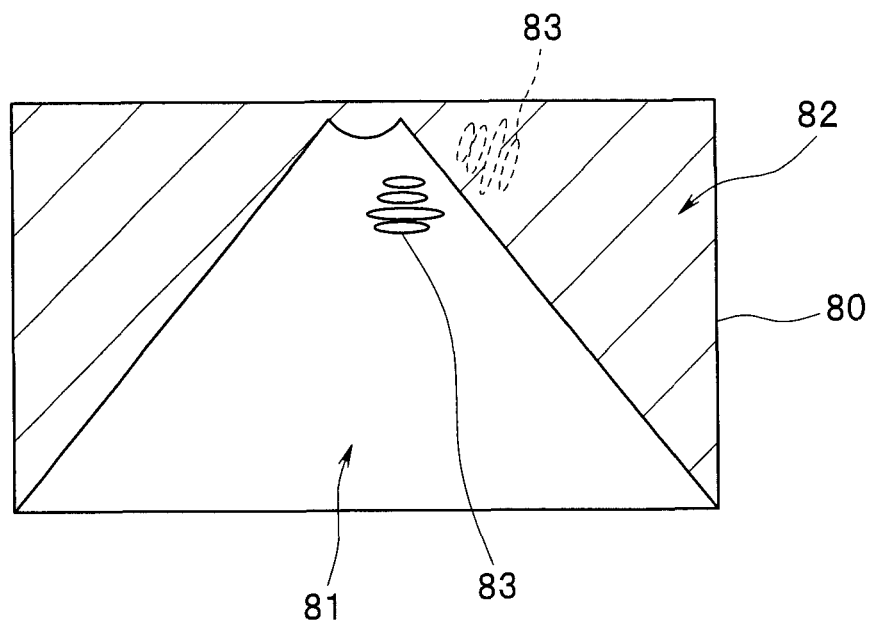
FIG. 14 is a view that illustrates an example in which a reflected image of a distal end face is displayed in a display image as the result of a side lobe of ultrasound that is radiated from the ultrasound transducer shown in FIG. 1 being reflected by a distal end face of a distal end portion of an insertion portion.
Figure 15:
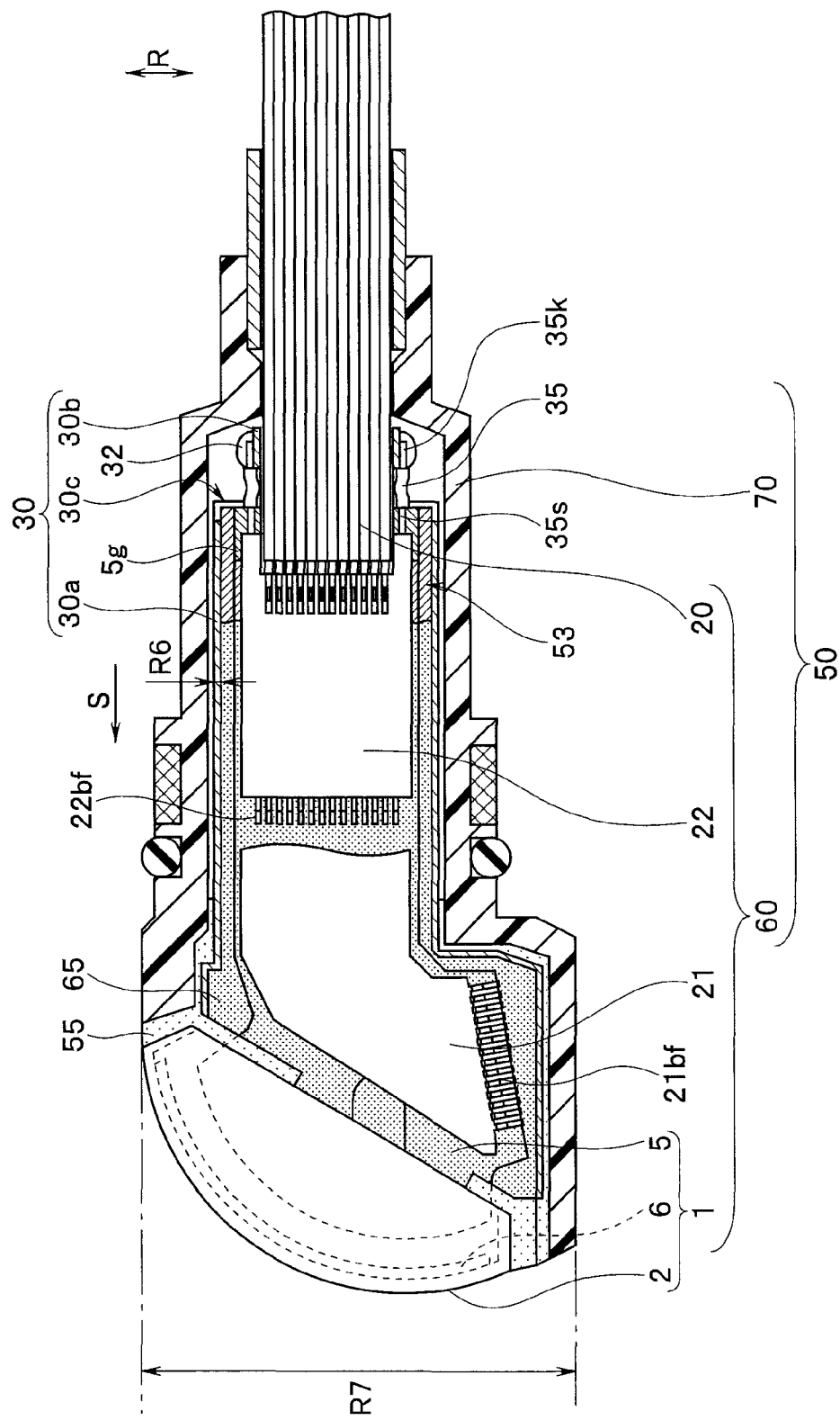
FIG. 15 is a partial cross-sectional view of an ultrasound transducer unit that illustrates an example in which the metal shield member shown in FIG. 1 is formed to be thinner than in FIG. 1.

FIG. 14 is a view that illustrates an example in which a reflected image of a distal end face is displayed in a display image as the result of a side lobe of ultrasound that is radiated from the ultrasound transducer shown in FIG. 1 being reflected by a distal end face of a distal end portion of an insertion portion. FIG. 15 is a partial cross-sectional view of an ultrasound transducer unit that illustrates an example in which the metal shield member shown in FIG. 1 is formed to be thinner than in FIG. 1.

Figure 16:
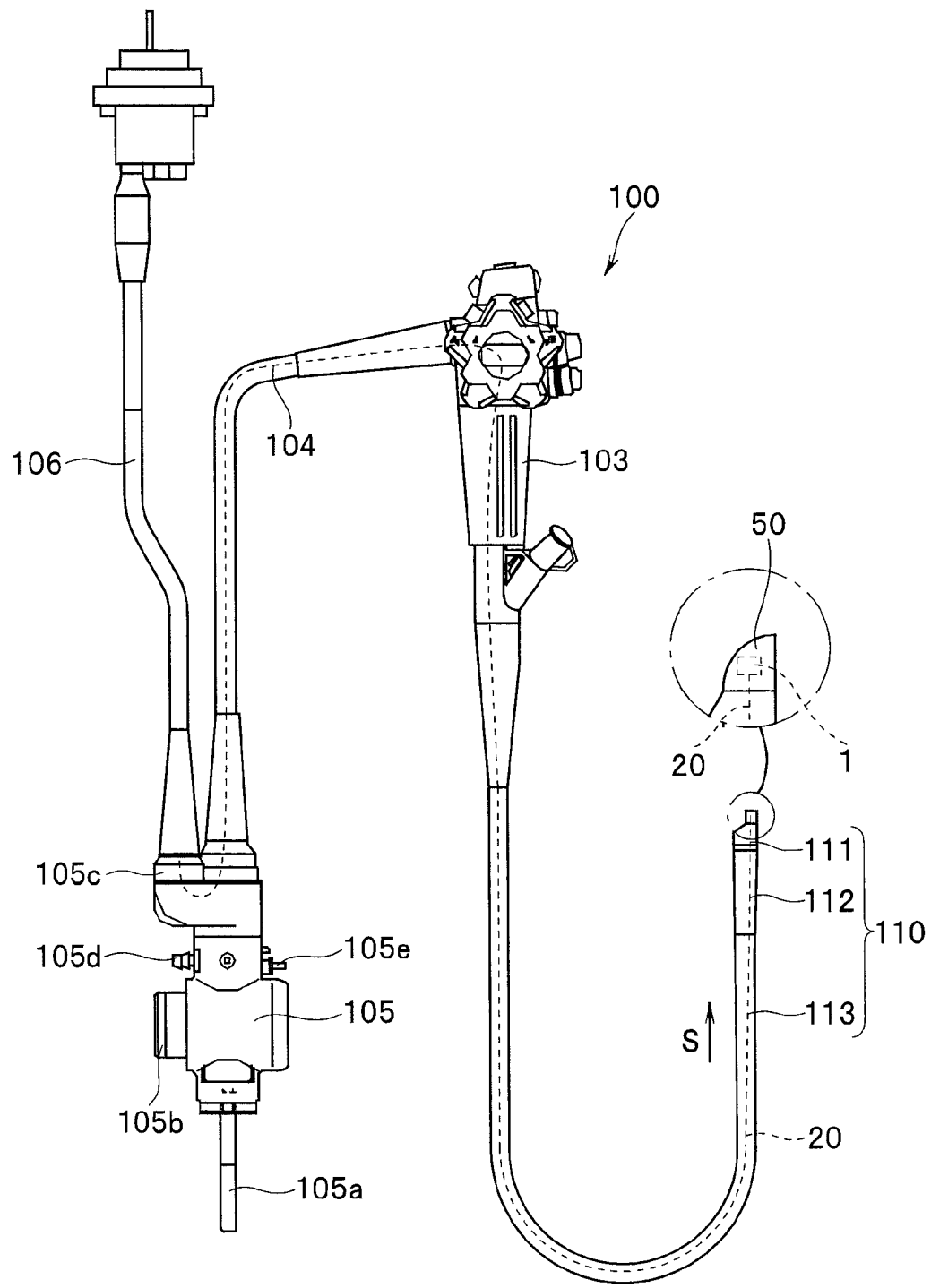
FIG. 16 shows the outer appearance of an ultrasound endoscope in which the ultrasound transducer unit shown in FIG. 3 is provided.

As shown in FIG. 1, a distal end portion 111 that is positioned at a distal end in an insertion direction S of an insertion portion 110 of an ultrasound endoscope 100 (the insertion portion 110 and ultrasound endoscope 100 are shown in FIG. 16) that are described later includes a distal end rigid member 40 that has a size R1 in a diameter direction R.

In the distal end rigid member 40, a distal end side in the insertion direction S of an ultrasound transducer unit 50 and a distal end side in the insertion direction S of a treatment instrument insertion channel 41 are provided along the insertion direction S. Note that the distal end side in the insertion direction S of the ultrasound transducer unit 50 has a diameter R2 in the diameter direction R.

As shown in FIG. 1, the ultrasound transducer unit 50 is provided so that, with respect to the distal end rigid member 40, the distal end thereof in the insertion direction S protrudes forward in the insertion direction S more than a distal end face 40s of the distal end rigid member 40. More specifically, at least an ultrasound element 6 such as a piezoelectric element that is included in an ultrasound transducer 1 is provided so as to protrude forward in the insertion direction S more than the distal end face 40s of the distal end rigid member 40.

An image pickup unit and an illumination unit (neither are shown in the drawings) are provided in the distal end rigid member 40. Further, a distal end side in the insertion direction S of an unshown air/water supply conduit and a forward water supply conduit 44 (see FIG. 2) or the like is provided along the insertion direction S.

In addition, as shown in FIG. 2, an objective optical system 42 that is included in the image pickup unit, and an illumination optical system 43 that is included in the illumination unit are provided in the distal end face 40s. Further, the distal ends in the insertion direction S of the treatment instrument insertion channel 41 and the forward water supply conduit 44 are opened at the distal end face 40s. Furthermore, an air/water supply nozzle 48 or the like that is fixed to the distal end of the air/water supply conduit that supplies a fluid to the objective optical system 42 is provided in the distal end face 40s.

Note that, preferably, the distal end face 40s is made from a material having an acoustic impedance that is substantially equal to the acoustic impedance of water, such as, for example, silicone rubber.

As shown in FIG. 1, in some cases, ultrasound that is radiated towards a site to be examined through acoustic matching layers 11 and 12 and a lens 2 (see FIG. 5), described later, from the ultrasound element 6 is also radiated in side lobe directions b in addition to being radiated in a main lobe direction a. Consequently, the ultrasound is also radiated towards the distal end face 40s.

Hence, if the acoustic impedance value of the material that the distal end face 40s is made of differs significantly from the acoustic impedance value of water, that is, the acoustic impedance value of a site in a living body as a site to be examined, ultrasound that is radiated in the side lobe directions b is liable to be reflected by the distal end face 40s, and unwanted scanning signals will be inputted to each ultrasound element 6. As a result, as shown in FIG. 14, there is the possibility that, on a display apparatus, a reflected image 83 which is normally not displayed because the reflected image 83 appears in a non-display region 82, will be displayed on the display apparatus as a virtual image in a display region 81 as the result of a known grating lobe after image processing.

Therefore, if the distal end face 40s is made from a material having an acoustic impedance that is substantially equal to water, that is, a living body, as shown in FIG. 14, it is possible to suppress the display of the reflected image 83 as a virtual image in the display region 81.

The above described situation is not limited to the distal end face 40s, and it is also preferable that in the distal end rigid member 40, an area at which ultrasound that is radiated in the side lobe directions b is reflected is made from a material having an acoustic impedance that is substantially equal to that of water.

Further, when a cover is covered over an outer surface of the distal end rigid member 40, it is preferable that the cover itself is made from a material having an acoustic impedance that is substantially equal to that of water.

As shown in FIG. 1, the ultrasound transducer unit 50 includes the ultrasound transducer 1. As shown in FIG. 4 and FIG. 5, the principal components of the ultrasound transducer 1 include the lens 2, a backing material frame 10, a substrate 5, a plurality of ultrasound elements 6, GND electrodes 15, signal electrodes 16, and acoustic matching layers 11 and 12.

More specifically, in the ultrasound transducer 1, the backing material frame 10 is provided on the inner side of the lens 2. Note that the backing material frame 10 is formed with, for example, glass epoxy resin.

The backing material frame 10 is formed in a frame shape by two facing end boards 3 and two facing side boards 4 so that the shape thereof in a plan view is rectangular. A rear end side in an ultrasound radiation direction P is positioned so as to protrude from the inside of the lens 2.

As shown in FIG. 3, it is preferable that each end board 3 is slantingly provided relative to a central axis d in the array direction of the ultrasound elements 6 so that a rear end side thereof in the ultrasound radiation direction P inclines to the inner side.

This is because, as shown in FIG. 4 and FIG. 5, in a case where each end board 3 is provided in parallel with the central axis d in the array direction, the diameter of the ultrasound transducer 1 will increase in the diameter direction R as the central axis d in the array direction inclines so as to become parallel to the insertion direction S. Furthermore, in comparison to a case where each end board 3 is provided in parallel with the central axis d in the array direction, when a configuration is adopted in which each end board 3 is slantingly provided as shown in FIG. 3, an outer diameter of the backing material frame 10 decreases towards the rear in the ultrasound radiation direction P. As a result, the diameter of the distal end side in the insertion direction S of the ultrasound transducer unit 50 in the diameter direction R can be reduced.

Hence, by adopting a configuration in which, in conformity with the end boards 3, both end faces 2v of the lens 2 are also formed in a shape that inclines so as to be parallel to the end boards 3, for the same reasons as for the backing material frame 10, it is possible to make the diameter of the distal end side in the insertion direction S of the ultrasound transducer unit 50 in the diameter direction R smaller in conformity with the inclination of the end boards 3.

A distal end side in the ultrasound radiation direction P of the substrate 5 is inserted through the inside of the backing material frame 10. A backing material 9 is filled inside the backing material frame 10 so as to cover the outer circumference of the distal end side in the ultrasound radiation direction P of the substrate 5.

A plurality of signal wiring lands 5s and GND wiring lands 5g are formed on both surfaces that face the side boards 4 of the substrate 5.

More specifically, as shown in FIG. 11, the substrate 5 is formed of seven layers that include a first resin layer 5j, GND wire layers 5g constituting GND wiring lands that are formed on both faces of the first resin layer 5j, second resin layers 5q formed on faces on an opposite side to the first resin layer 5j of each GND wire layer 5g, and signal wire layers 5s constituting signal wiring lands that are formed on faces on an opposite side to the respective GND wire layers 5g of each second resin layer 5q.

Note that a plurality of the signal wire layers 5s are provided with a predetermined interval therebetween in a direction that is orthogonal to the direction in which the layers are formed on each other.

The GND wiring lands are formed at areas that are exposed from the second resin layer 5q in the GND wire layer 5g.

Each signal wiring land 5s of the substrate 5 is electrically connected to each signal electrode 16 provided on a face on a substrate 5 side of the plurality of ultrasound elements 6 through signal wiring wires 7 inside the backing material 9, respectively.

Note that connection portions between each signal wiring land 5s and each signal wiring wire 7 and connection portions between the signal electrodes 16 and each signal wiring wire 7 are covered by an unshown metal frame that is grounded to ensure electrical safety.

The ultrasound elements 6 are formed by firing a piezoelectric material, for example, ceramic, and are arranged, for example, in a convex shape.

The ultrasound elements 6 irradiate ultrasound through the acoustic matching layers 11 and 12 and the lens 2 at a site to be examined, and also receive acoustic waves that are reflected from the site to be examined.

Inside the lens 2, the GND electrodes 15 that have been subjected to a poling process are respectively provided on a front side in the ultrasound radiation direction P of each ultrasound element 6.

The GND electrodes 15 and the signal electrodes 16 cause the ultrasound elements 6 to vibrate by applying a pulse voltage that is transmitted through a signal transmission cable 20 (see FIG. 1) that is described later from an unshown controller to the ultrasound elements 6. Note that the respective GND electrodes 15 constitute an acoustic radiation face of the respective ultrasound elements 6. That is, in each ultrasound element 6, the GND electrode 15 is provided in a direction that faces the site to be examined.

In addition, in the lens 2, the acoustic matching layer 11 is provided at a more frontward position in the ultrasound radiation direction P than the GND electrode 15, and the acoustic matching layer 12 is provided at a more frontward position in the ultrasound radiation direction P than the acoustic matching layer 11.

In this case, with respect to the substrate 5, various operations are performed while the substrates remain in a large state because, since a holding property with respect to the substrates is favorable when the substrates are in a large state, it is easy to perform various operations when electrically connecting the ultrasound elements 6 and the signal wiring lands 5s by means of the signal wiring wires 7 or when forming the lens 2 or the like. Thereafter, the substrates are cut into a certain size so that each substrate 5 can be compactly housed inside a transducer case 70 (see FIG. 3) that is described later.

At the time of the aforementioned cutting operation, as shown in FIG. 3, when cutting is performed so that a lower end site 5u of the substrate 5 that is located in the vicinity of a site to which a distal end of a flexible substrate 21 that is described later is connected is positioned at a higher position in the diameter direction R than an end face 2v on an underside in FIG. 3 of the lens 2, that is, so as to position the lower end site 5u of the substrate 5 on the inner side so as to make the respective substrates 5 as small as possible, there have been cases in which a blade of an apparatus that cuts the substrates 5 strikes against the lens 2 and damages the lens 2. Hence, a configuration is desirable that can make the substrate 5 as small as possible without causing damage to the lens 2.

Therefore, according to the present embodiment, a cutting-plane line e that is used for forming the lower end site 5u of the substrate 5 is inclined at a predetermined angle with respect to the insertion direction S. More specifically, the cutting-plane line e is inclined at a predetermined angle so that an extension line towards the front in the insertion direction S of the cutting-plane line e is positioned so as to be lower than an extension line 2t of the end face 2v on the underside of the lens 2, and an extension line towards the rear in the insertion direction S of the cutting-plane line e is positioned so as to be higher than the extension line 2t of the end face 2v on the underside of the lens 2. That is, a configuration is adopted in which the lower end site 5u of the substrate 5 is formed by cutting the substrate 5 along the cutting-plane line e that is inclined at a predetermined angle.

Therefore, because the blade of the cutting apparatus does not contact the lens 2 and, in addition, the lower end site 5u after cutting can be positioned, as much as possible, at a higher position than the end face 2v on the underside of the lens 2, that is, can be positioned on the inner side in the diameter direction R, the substrate 5 can be formed as small as possible, and hence a reduction in the size of the ultrasound transducer 1 can be achieved.

Further, as shown in FIG. 4 and FIG. 5, at an area that protrudes to the rear in the ultrasound radiation direction P from the backing material frame 10 of the substrate 5, the GND wiring lands 5g are formed on both faces on which the signal wiring lands 5s are formed facing the respective side boards 4.

One end of each of a plurality of connection wires 8 is electrically connected by a solder or the like to the GND wiring lands 5g of the substrate 5. The other end of each of the plurality of connection wires 8 is electrically connected by a solder or the like to a conductive film 91 that is formed by attaching copper foil or the like to the surface of an area that protrudes from the lens 2 of each end board 3.

More specifically, each GND wiring land 5g of the substrate 5 is electrically connected to the conductive film 91 through the connection wires 8. Thus, the configuration is one in which the end boards 3 are grounded. Note that, although not shown in the drawings, the conductive film 91 is also formed at the side boards 4, and the side boards 4 are also grounded.

Note that, conventionally, with respect to the electrical connection of the other end of the respective connection wires 8 to the conductive film 91 of each end board 3, a configuration has been used in which a through-hole is provided in each end board 3, and the other end of each connection wire 8 is electrically connected by a solder or the like to the conductive film 91 inside the through-hole. However, according to that conventional configuration, since it is necessary to perform connection work inside the through-holes, there is the drawback that it is difficult to perform the connection work and that the connection strength is weak.

Therefore, according to the present embodiment, as shown in FIG. 4 and FIG. 5, a configuration is used in which, at the area that protrudes from the lens 2 of each end board 3, a plurality of concave portions 3h that penetrate the relevant end board 3 along an extending direction of the GND wiring lands 5g as shown in FIG. 4 are provided in a rear end face in the ultrasound radiation direction P, and at a bottom face 3ht of each of the concave portions 3h, the other end of each connection wire 8 is electrically connected by a solder or the like to the conductive film 91 that is formed on the bottom face 3ht. Hence, a configuration is used in which the other end of each connection wire 8 can be electrically connected to the conductive film 91 easily and securely from the rear in the ultrasound radiation direction P.

Further, as shown in FIG. 3, at an area that protrudes to the rear in the ultrasound radiation direction P from the backing material frame 10 of the substrate 5, distal ends of flexible substrates 21 and 22 are electrically connected to each signal wiring land 5s and GND wiring land 5g of the substrate 5, and a distal end of the signal transmission cable 20 that is used to transfer at least electric power and electrical signals to and from the ultrasound elements 6 is electrically connected to the proximal end side of each of the flexible substrates 21 and 22.

Hereunder, a structure in which the flexible substrates 21 and 22 are connected to the ultrasound transducer 1, and the signal transmission cable 20 is connected to the flexible substrates 21 and 22 is referred to as "ultrasound transducer module 60."

More specifically, as shown in FIG. 9, at a position that is more forward in the insertion direction S than the distal ends of two of the flexible substrates 22, the distal ends of two of the flexible substrates 21 are electrically connected in the vicinity of the above described lower end site 5u of the substrate 5 to signal wiring lands 5s on both faces that face the side boards 4 at the area that protrudes from the backing material frame 10 of the substrate 5.

This is because when a configuration is used in which the respective distal ends of the flexible substrates 21 and 22 are electrically connected on both faces of the substrate 5, even if a number of signal lines 21b and 22b (see FIG. 10) that are described later of the flexible substrates 21 and 22 increases, the size of the ultrasound transducer module 60 can be reduced in comparison to a configuration in which the respective distal ends of the flexible substrates 21 and 22 are electrically connected on only one face of the substrate 5.

Further, as shown in FIG. 9, the distal ends of the flexible substrates 22 are electrically connected to the signal wiring lands 5s of the substrate 5 so that rear ends of the flexible substrates 21 overlap only at a region M in the insertion direction S with the distal ends of the flexible substrates 22.

The reason for adopting this configuration is that the ultrasound transducer module 60 can be shortened in the insertion direction S by providing the overlapping region M. That is, this configuration is adopted to enable a reduction in the size of the ultrasound transducer module 60.

In other words, if a configuration is used in which the overlapping region M is not provided, and which electrically connects the distal ends of the flexible substrates 21 to the signal wiring lands 5s of the substrate 5 at a position that is more forward in the insertion direction S than the distal ends of the flexible substrates 22, the length of the ultrasound transducer module 60 will increase in the insertion direction S.

Hence, it is preferable that the overlapping region M can be secured over as long as possible an area in the insertion direction S in order to reduce the size of the ultrasound transducer module 60.

Next, a specific configuration for connecting the distal ends of the flexible substrates 21 and 22 to the signal wiring land 5s and the GND wiring lands 5g on both faces of the substrate 5 is described using FIG. 10 and FIG. 11. Note that, to simplify the drawings, FIG. 10 and FIG. 11 illustrate a configuration in which the distal ends of flexible substrates 21 and 22 are connected to one face of the substrate 5.

As shown in FIG. 10 and FIG. 11, the flexible substrates 21 and 22 are formed from five layers that include resin layers 21a and 22a, a layer in which the signal lines 21b and 22b are formed that is formed on one face of the resin layer 21a, resin layers 21c and 22c formed on a face on an opposite side to the resin layers 21a and 22a of the signal lines 21b and 22b, a layer in which GND lines 21d and 22d are formed that is formed on an opposite side to the signal lines 21b and 22b of the resin layers 21c and 22c, and resin layers 21e and 22e formed on an opposite side to the resin layers 21c and 22c of the GND lines 21d and 22d. Note that the resin layers 21a, 22a, 21e, and 22e constitute an outer covering of the respective flexible substrates 21 and 22.

Further, the reason the layer with the GND lines 21d and 22d is provided in the flexible substrates 21 and 22, respectively, is to use the GND lines 21d and 22d to prevent the generation of so-called "crosstalk" that is the unintended exchange of signals between the signal lines 21b and 22b and the signal wire layer 5s that may occur if the signal lines 21b and 22b are adjacent to the signal wire layer 5s of the substrate 5.

More specifically, by providing the GND lines 21d and 22d, as shown in FIG. 10, not only can the signal lines 21b and 22b be sufficiently separated by the amount of a space H from the signal wire layer 5s, but in addition, because the GND lines 21d and 22d are grounded, it is difficult for crosstalk to arise between the signal lines 21b and 22b and the signal wire layer 5s. That is, the GND lines 21d and 22d function as a shield layer. It is thereby possible to reduce noise that arises in a display of an ultrasound image that is caused by crosstalk.

A plurality of the signal lines 21b and 22b protrude forward as flying leads 21bf and 22bf from the respective distal ends of the flexible substrates 21 and 22. As shown in FIG. 9 and FIG. 10, each of the flying leads 21bf and 22bf is electrically connected by a solder 99 to the signal wire layer 5s that serves as the respective signal wiring lands 5s of the substrate 5.

Further, as shown in FIG. 11, the GND lines 21d and 22d also protrude forward as flying leads 21df and 22df from the respective distal ends of the flexible substrates 21 and 22. Each of the flying leads 21df and 22df is electrically connected by an unshown solder or the like to the GND wire layer 5g that serves as a GND wiring land of the substrate 5.

According to this configuration, the distal ends of the flexible substrates 21 and 22 are connected to the signal wiring lands 5s and the GND wiring lands 5g on both faces of the substrate 5.

In addition, as shown in FIG. 9, distal ends of the signal transmission cable 20 are electrically connected to the rear ends of the flexible substrates 21 and 22, respectively, by solders 23 and 24.

More specifically, the signal transmission cable 20 includes a plurality of cables, and as shown in FIG. 8, each cable is constituted by a coaxial line in which a resin jacket 20b is covered over the outer circumference of a signal wire 20a, a GND wire 20c is covered over the outer circumference of the resin jacket 20b, and a resin jacket 20d is covered over the outer circumference of the GND wire 20c.

As shown in FIG. 7, each coaxial line of the signal transmission cable 20 has a configuration in which, at the distal end in the insertion direction S of the signal transmission cable 20, the GND wire 20c protrudes forward in the insertion direction S more than the distal end in the insertion direction S of the resin jacket 20d, the distal end in the insertion direction S of the resin jacket 20b protrudes forward in the insertion direction S more than the distal end in the insertion direction S of the GND wire 20c, and the distal end in the insertion direction S of the signal wire 20a protrudes forward in the insertion direction S more than the distal end in the insertion direction S of resin jacket 20b.

Each of the protruding signal wires 20a is electrically connected by a solder 23 or 24 or the like to a pattern of the signal lines 21b and 22b of the flexible substrates 21 and 22. Further, each of the protruding GND wires 20c is electrically connected by an unshown solder or the like to a pattern of the GND lines 21d and 22d of the flexible substrates 21 and 22. Thus, the respective distal ends of the signal transmission cable 20 are electrically connected to the rear ends of the flexible substrates 21 and 22.

Hence, the signal transmission cable 20 has a function that transfers various kinds of electrical signals or electric power to and from the ultrasound elements 6 through the signal lines 21b and 22b of the flexible substrates 21 and 22 and the signal wiring lands 5s, the signal wiring wires 7, and the signal electrodes 16 of the substrate 5.

Further, the signal transmission cable 20 is also grounded together with the conductive film 91 of the backing material frame 10 through the GND wires 20c, the GND lines 21d and 22d, the GND wiring lands 5g and the connection wires 8.

As shown in FIG. 1 and FIG. 3, the ultrasound transducer module 60 that has the above described configuration is held by the transducer case 70 inside the distal end rigid member 40. Note that the transducer case 70 is made from, for example, resin.

Further, inside the transducer case 70, a metal shield member 30 is provided so as to cover the outer circumference of the substrate 5. A distal end side in the insertion direction S of the metal shield member 30 is fixed by an adhesive 55 composed of, for example, an insulating resin or the like to the transducer case 70 and the lens 2.

Further, the metal shield member 30 is fixed to the substrate 5 by an adhesive 65 composed of, for example, an insulating resin or the like that is filled inside a large-diameter portion 30a that is described later of the metal shield member 30.

Note that, in the present embodiment, a structure in which the metal shield member 30 and the transducer case 70 are provided in the ultrasound transducer module 60 is taken to be the ultrasound transducer unit 50.

The metal shield member 30 is formed from a cylindrical member. As shown in FIG. 3 and FIG. 6, the metal shield member 30 includes, as principal components, a large-diameter portion 30a having a diameter of R10, a small-diameter portion 30b that has a diameter of R11 that is smaller than the diameter of the large-diameter portion (R11<R10) and that is positioned more to the rear than the large-diameter portion 30a in the direction in which the ultrasound elements 6 and the signal transmission cable 20 are connected, that is, in the insertion direction S, and a step portion 30c that connects the large-diameter portion 30a and the small-diameter portion 30b in the insertion direction S. In the metal shield member 30, the large-diameter portion 30a covers the outer circumference of the substrate 5, and the small-diameter portion 30b covers the outer circumference on the distal end side in the insertion direction S of the signal transmission cable 20.

Note that, as the process for providing the metal shield member 30 and the transducer case 70, a process is used in which, first, the metal shield member 30 is disposed so that the large-diameter portion 30a covers the outer circumference of the substrate 5 of the ultrasound transducer module 60, thereafter, the adhesive 65 is filled from the forward side in the insertion direction S of the metal shield member 30 to fix the substrate 5 to the large-diameter portion 30a, and next, the transducer case 70 is covered over the outer circumference of the metal shield member 30 and is fixed to the metal shield member 30 by the adhesive 55.

However, since there are gaps between the respective coaxial lines of the signal transmission cable 20, when the adhesive 65 is filled from the front into the metal shield member 30, there is a possibility that the adhesive 65 will leak from between the coaxial lines of the signal transmission cable 20 and generate a cavity inside the large-diameter portion 30a.

Hence, according to present embodiment, as shown in FIG. 3, when covering the metal shield member 30 over the outer circumference of the ultrasound transducer module 60, a process is used in which the metal shield member 30 and the outer circumference of an area that is inserted into the metal shield member 30 of the signal transmission cable 20 are temporarily fixed in advance using an adhesive 53 for temporary fixing such as a quick-drying adhesive or a high-viscosity adhesive, and thereafter the adhesive 65 is filled from the front into the metal shield member 30.

More specifically, the ultrasound transducer unit 50 has a configuration in which the metal shield member 30 and the outer circumference of an area that is inserted into the metal shield member 30 of the signal transmission cable 20 are adhesively fixed together by the adhesive 53.

Note that an adhesive that contains metal filler that is not electrically conductive ($SiO_2$, $Al_2O_3$, $CaCO_3$) or the like may be used as the adhesive 53 for temporary fixing.

According to this configuration, a gap does not arise between the metal shield member 30 and the signal transmission cable 20, and hence, in the process thereafter, even when the adhesive 65 is filled into the metal shield member 30, the adhesive 65 does not leak out from between the coaxial lines of the signal transmission cable 20. Thus, in this configuration, the adhesive 65 fixes the metal shield member 30 while reliably ensuring insulation of the substrate 5.

Further, as shown in FIG. 1, the large-diameter portion 30a of the metal shield member 30 has a maximum diameter portion 30am on the distal end side in the insertion direction S.

Note that since an area on the ultrasound elements 6 side of the substrate 5 is large because the central axis d in the array direction of the ultrasound elements 6 is inclined, the maximum diameter portion 30am is formed in the large-diameter portion 30a to cover the aforementioned large area of the substrate 5.

In this case, there was the problem that if the central axis of the maximum diameter portion 30am and a central axis 20i of the signal transmission cable 20 and another area of the large-diameter portion 30a are matching, the ultrasound transducer unit 50 will increase in the diameter direction R by an amount corresponding to the size of the maximum diameter portion 30am, and in addition, a dead space will arise between the ultrasound transducer unit 50 and another member inside the distal end rigid member 40, and the diameter of the distal end rigid member 40 will increase.

Hence, according to the present embodiment, the maximum diameter portion 30am is provided inside the transducer case 70 so that, in the diameter direction R, a central axis 30i is shifted to a lower side in FIG. 1 than the central axis 20i of the signal transmission cable 20 and another area of the large-diameter portion 30a.

Thus, inside the distal end rigid member 40, a dead space that arises between the ultrasound transducer unit 50 and another member is decreased, and hence, even when the maximum diameter portion 30am is provided in the large-diameter portion 30a, the diameter R1 of the distal end rigid member 40 can be reduced without changing the diameter R2 on the distal end side in the insertion direction S of the ultrasound transducer unit 50.

The description will now return to FIG. 3 and FIG. 6. As shown in FIG. 3 and FIG. 6, an opening portion 33 is formed in the step portion 30c of the large-diameter portion 30a of the metal shield member 30. Note that a configuration may also be adopted in which the opening portion 33 is formed in only the small-diameter portion 30b.

Inside the large-diameter portion 30a, one end 35s of the ground wiring 35 is electrically connected by a solder or the like to the GND wiring land 5g of the substrate 5. The other end 35k of the ground wiring 35 extends to outside the large-diameter portion 30a, that is, to outside the metal shield member 30, through the opening portion 33 and is electrically connected by a solder 32 or the like to an outer circumferential face 30g on an opposite side to an inner surface 30n of the small-diameter portion 30b. As a result, the metal shield member 30 is grounded.

Note that, since the metal shield member 30 is securely grounded, even if the adhesive 55 that is adhered to the end face 2v of the lens 2 becomes detached therefrom and an electrically conductive fluid such as water that contains impurities from inside the body enters into the transducer case 70, since the configuration is such that it is easy for the electrically conductive fluid to come in contact with the grounded metal shield member 30 before contacting conducting portions inside the ultrasound transducer unit 50, such as connection portions between the substrate 5 and the flexible substrates 21 and 22, the electrical safety is secured.

Note that, in view of this fact, it is desirable that the above described backing material frame 10 is also grounded, and not only the metal shield member 30. This is because a fluid that enters from the vicinity of the end face 2v of the lens 2 will invariably come in contact with the backing material frame 10.

Therefore, as described above, since the conductive film 91 is formed on the backing material frame 10, and the conductive film 91 is electrically connected through the connection wires 8 with the GND wiring lands 5g of the substrate 5, the present embodiment has a configuration in which the backing material frame 10 is grounded.

In addition, with respect to the grounding structure of the metal shield member 30, as shown in FIG. 13, a configuration has conventionally been used in which the cylindrical metal shield member 30 covers as far as a proximal end in the insertion direction S of the substrate 5 and the other end 35k of the ground wiring 35 that has the one end 35s electrically connected to the GND wiring land 5g of the substrate 5 is routed as far as the outer circumferential face 30g of the metal shield member 30 from an opening at the proximal end in the insertion direction S of the metal shield member 30, and is electrically connected by a solder 32 or the like to the outer circumferential face 30g.

Hence, according to the above described configuration that is shown in FIG. 13, since it is necessary to secure space inside the transducer case 70 for a connection site between the other end 35k of the ground wiring 35 and the outer circumferential face 30g of the metal shield member 30, there has been the problem that a diameter R9 of the inner surface of the transducer case 70 in the diameter direction R increases by an amount corresponding to the space required for the connection site, that is, the size of the ultrasound transducer unit 50 increases in the diameter direction R.

However, in the configuration shown in FIG. 3, since the other end 35k of the ground wiring 35 is led out to outside the metal shield member 30 through the opening portion 33 from inside the large-diameter portion 30a, and the other end 35k is electrically connected to the small-diameter portion 30b that has a smaller diameter than the large-diameter portion 30a, a diameter R3 of the inner surface of the transducer case 70 in the diameter direction R can be made smaller than the diameter R9 of the inner surface of the transducer case 70 shown in FIG. 13 (R3<R9). More specifically, the diameter of the ultrasound transducer unit 50 can be made smaller than the diameter shown in FIG. 13.

The metal shield member 30 ensures the electrical insulation of various connection sites by covering the outer circumference of the above described connection sites between the substrate 5 and the distal ends of the respective flexible substrates 21 and 22 and the above described connection sites between the distal ends of the signal transmission cable 20 and the respective flexible substrates 21 and 22, together with the insulating adhesive 65.

As shown in FIG. 12, inside a transducer case 70 in an ultrasound transducer unit 50', by making a wall thickness R16 of the transducer case 70 greater than a wall thickness R15 of the transducer case 70 shown in FIG. 3 (R15<R16), the electrical insulation can be ensured even without covering the outer circumference of the substrate 5 with the metal shield member 30, and the withstand voltage performance can be improved.

However, in the configuration shown in FIG. 12, since the outer diameter R4 of the ultrasound transducer unit 50' becomes larger in the diameter direction R than the outer diameter R2 of the ultrasound transducer unit 50 in the configuration using the metal shield member 30 as shown in FIG. 3 (R2<R4), the configuration shown in FIG. 12 is not preferable.

More specifically, in the configuration that ensures the electrical insulation of various connection sites with respect to the substrate 5 and the flexible substrates 21 and 22 using the metal shield member 30 as shown in FIG. 3 according to the present embodiment, with respect to the ultrasound transducer 1, since there are no portions that are not covered with a grounded member, a withstand voltage that is required from the viewpoint of electrical safety is low. Hence the wall thickness R15 of the transducer case 70 according to the present embodiment can be formed to be thinner in the diameter direction R than the wall thickness R16 of the transducer case 70 shown in FIG. 12 (R15<R16), and the outer diameter R2 of the ultrasound transducer unit 50 can be made smaller in the diameter direction R than the outer diameter R4 of the ultrasound transducer unit 50' shown in FIG. 12 (R2<R4).

Further, with regard to configurations that do not use the metal shield member 30, as a configuration that ensures electrical safety without thickening the wall thickness of the transducer case 70, a configuration is known in which metal is applied onto the inner surface of the transducer case 70 by coating or plating or the like.

According to this configuration, since the wall thickness of the transducer case 70 is not made thick, and further, the metal shield member 30 need not be used, the outer diameter of the ultrasound transducer unit 50 can be reduced. However, according to this configuration, at the time of coating or plating, there are cases where the inner surface of the transducer case 70 is subjected to thermal damage, or is subjected to chemical damage that is caused by treatment using a chemical, and therefore the aforementioned configuration is not preferable.

Hence, in the present embodiment a configuration is adopted that uses the metal shield member 30, and it is necessary to form the metal shield member 30 as thinly as possible to prevent the outer diameter of the ultrasound transducer unit 50 increasing due to the metal shield member 30.

In view of the aforementioned circumstances, by forming the metal shield member 30 by a known electroforming process that uses Ni, Cu, Au or the like, as shown in FIG. 15, a wall thickness R6 of the metal shield member 30 can be formed with a uniform film thickness that is thinner than the wall thickness R5 of the metal shield member 30 shown in FIG. 3 (R6<R5). Hence, the outer diameter R7 of the ultrasound transducer unit 50 can be made smaller than the outer diameter R2 of the ultrasound transducer unit shown in FIG. 3 (R7<R2). Further, since it is not necessary to perform plating or the like with respect to the inner surface of the transducer case 70, damage is not caused to the transducer case 70.

In addition, if the metal shield member 30 is formed by an electroforming process, the metal shield member 30 can be formed in a small size, and can be precisely formed in a manner in which there are few dimensional configurations.

Thus, according to the present embodiment a configuration has been described in which, in the ultrasound transducer unit 50, the metal shield member 30 that covers the outer circumference of the substrate 5 inside the transducer case 70 includes the large-diameter portion 30a, the small-diameter portion 30b, and the step portion 30c. Further, in the aforementioned configuration, the metal shield member 30 is grounded by leading out the other end 35k of the ground wiring 35 having the one end 35s electrically connected to the GND wiring land 5g of the substrate 5 to outside the metal shield member 30 from inside the large-diameter portion 30a through the opening portion 33 that is formed in the step portion 30c or the small-diameter portion 30b and electrically connecting the other end 35k to the outer circumferential face 30g of the small-diameter portion 30b that has a smaller diameter than the large-diameter portion 30a.

According to this configuration, by electrically connecting the other end 35k to the outer circumferential face 30g of the small-diameter portion 30b, accompanying the connection of the other end 35k to the metal shield member 30, the connection site of the other end 35k does not protrude to the outer side in the diameter direction R more than the large-diameter portion 30a that has the largest diameter within the metal shield member 30. Hence, as shown in FIG. 3, the diameter R3 of the inner surface of the transducer case 70 in the diameter direction R can be made smaller than the diameter R9 of the inner surface of the transducer case 70 shown in FIG. 13 that has been conventionally used (R3<R9). That is, the outer diameter of the ultrasound transducer unit 50 can be made smaller than the outer diameter of the conventional ultrasound transducer unit that is shown in FIG. 13.

In addition, inside the transducer case 70, the metal shield member 30, together with the insulating adhesive 65, covers the connection sites of the flexible substrates 21 and 22 with respect to the substrate 5 and the connection sites of the signal transmission cable 20 with respect to the flexible substrates 21 and 22 in a reliable manner. Hence, the electrical insulation of the various connection sites can be ensured.

As described above, the ultrasound transducer unit 50 is provided, for example, in the ultrasound endoscope 100. Hereunder, the configuration of the ultrasound endoscope in which the ultrasound transducer unit 50 is provided is described using FIG. 16.

FIG. 16 is a view that shows the outer appearance of an ultrasound endoscope in which the ultrasound transducer unit shown in FIG. 3 is provided.

The principal components of the ultrasound endoscope 100 include an elongated insertion portion 110 that is inserted into a subject, an operation portion 103 provided at a proximal end in the insertion direction S of the insertion portion 110, a flexible universal cord 104 that extends from the operation portion 103, and a connector 105 that is provided at an extending end of the universal cord 104.

A light source connector 105a, an electrical connector 105b, an ultrasound connector 105c, a suction pipe sleeve 105d, and an air/water supply pipe sleeve 105e are provided in the connector 105.

A light source apparatus that supplies illuminating light is detachably connected to the light source connector 105a, and a video processor that performs various kinds of signal processing and the like is detachably connected through a signal cable to the electrical connector 105b.

Further, an ultrasound observation apparatus is detachably connected to the ultrasound connector 105c through an ultrasound cable 106 that is connected to the ultrasound observation apparatus. A suction pump is detachably connected through a suction tube to the suction pipe sleeve 105d. In addition, a water supply tank is detachably connected through an air/water supply tube to the air/water supply pipe sleeve 105e.

The insertion portion 110 includes a distal end portion 111, a bending portion 112 that is configured to be bendable in, for example, in the vertical and lateral directions, and a flexible tube portion 113 that is long and has flexibility. The aforementioned portions are connected in series in that order from the distal end side in the insertion direction S of the insertion portion 110.

The signal transmission cable 20 that is extended from the flexible substrates 21 and 22 of the ultrasound transducer 1 at the distal end portion 111 is inserted through the insertion portion 110, the operation portion 103, and the universal cord 104 as far as the ultrasound connector 105c of the connector 105, and is electrically connected to the ultrasound cable 106 by the ultrasound connector 105c.

Note that, the configuration of the ultrasound endoscope 100 that is shown in FIG. 16 as described above is merely one example, and the present invention is not limited thereto.

Thus, the ultrasound transducer unit 50 and the ultrasound endoscope 100 can be provided that can ensure electrical safety and in which a smaller diameter can be realized.

Note that although according to the foregoing embodiment an example is described in which the signal transmission cable 20 is electrically connected to the substrate 5 through the flexible substrates 21 and 22, a configuration may also be adopted in which the signal transmission cable 20 is electrically connected to the substrate 5 directly, without using the flexible substrates 21 and 22.

Further, although according to the foregoing embodiment an example is described in which the ultrasound elements 6 are used as the ultrasound elements in an ultrasound transducer, a configuration may also be adopted in which a capacitive micromachined ultrasonic transducer (C-MUT) element that includes a pair of electrodes that face each other in a manner that sandwiches an air gap therebetween is used instead of the ultrasound element 6.

What is claimed is:

1. An ultrasound transducer unit, comprising:
   an ultrasound element;
   a substrate having one end that is electrically connected to the ultrasound element;
   a signal transmission cable that is electrically connected to the other end of the substrate;
   a cylindrical metal shield member having a large-diameter portion, a small-diameter portion that has a smaller diameter than a diameter of the large-diameter portion, and a step portion that connects the large-diameter portion and the small-diameter portion, in which an opening portion is formed in the step portion or the small-diameter portion, and in which the large-diameter portion covers an outer circumference of the substrate; and
   ground wiring that electrically connects the substrate and an outer circumferential face of the metal shield member on an opposite side to an inner surface that faces the substrate;
   wherein,
   the ground wiring electrically connects the substrate and the outer circumferential face of the metal shield member by being extended to outside the metal shield member from inside the large-diameter portion of the metal shield member through the opening portion and electrically connected to the outer circumferential face of the small-diameter portion.

2. The ultrasound transducer unit according to claim 1, wherein, the large-diameter portion is positioned further to the ultrasound element side than the small-diameter portion in a direction in which the ultrasound element and the signal transmission cable are connected by the substrate.

3. An ultrasound endoscope, comprising the ultrasound transducer unit according to claim 1 at a distal end in an insertion direction of an insertion portion that is inserted into a subject.

* * * * *